United States Patent [19]

Burnouf-Radosevich et al.

[11] Patent Number: 5,252,217
[45] Date of Patent: Oct. 12, 1993

[54] BLOOD COAGULATION FACTOR XI CONCENTRATE HAVING HIGH SPECIFIC ACTIVITY, SUITABLE FOR THERAPEUTIC USE, AND PROCESS FOR PREPARING SAME

[75] Inventors: Miryana Burnouf-Radosevich, Wavrin; Dominique Dernis, Marquette-lez-Lille, both of France

[73] Assignee: Association pour l'Essor de la Transfusion Sanguine dans la Region du Nord, Lille, France

[21] Appl. No.: 879,273

[22] Filed: May 7, 1992

[30] Foreign Application Priority Data

May 7, 1991 [FR] France ................... 91 05572

[51] Int. Cl.$^5$ ............................... B01D 15/08
[52] U.S. Cl. ...................... 210/635; 210/656; 435/13; 436/69; 530/381; 530/416; 530/417
[58] Field of Search ............... 210/635, 656, 198.2; 435/13; 436/69; 530/381, 416, 417

[56] References Cited

U.S. PATENT DOCUMENTS 4,783,262  11/1988  Ostreicher et al. ............... 210/314
4,859,340   8/1989  Hou et al. ....................... 210/502.1

OTHER PUBLICATIONS

Journal of Bio. Chem., vol. 252, No. 18 (1977), pp. 6432-6437: Bouma et al.: Human Blood Coagulation Factor XI . . .

Throm. Res. 60; 87-97 (1990): Schiffman et al.: Purification and Characterization of Platelet Factor XI.

Winkelman et al. International Congress ISBT-BBTS, London, Jul. 1988: Production and Clinical Use of a Therapeutic Concentrate of Factor XI from Human Plasma Abstract #P-M-4-15.

Zeta Plus S Series Filter Media, Cuno Inc. 1990, pp. 1-6 Article #ZP, S01., 0490.

Zeta Plus Publication #ZP S01. 1288, Cuno Inc. 1988, pp. 5-13.

Biological Abstracts, vol. 65, Ref. 12893 (1978): Bouma et al. "Human blood Coagulation Factor XI".

Methods in Enzymology/Blood Clotting Enzymes pp. 65-73 (1975).

*Primary Examiner*—Ernest G. Therkorn
*Attorney, Agent, or Firm*—Birch, Stewart, Kolasch & Birch

[57] ABSTRACT

The invention relates to a human Factor XI concentrate having high specific activity prepared using a process comprising a filtration-adsorption step and a single step of chromatography on cation exchange resin.

The concentrate obtained is perfectly suitable for therapeutic use in replacement therapy in cases of Factor XI deficiency.

13 Claims, No Drawings

BLOOD COAGULATION FACTOR XI CONCENTRATE HAVING HIGH SPECIFIC ACTIVITY, SUITABLE FOR THERAPEUTIC USE, AND PROCESS FOR PREPARING SAME

BACKGROUND OF THE INVENTION

1. Field of the Invention

The invention relates to a process for preparing a concentrate of human plasma Factor XI having very high specific activity and intended for therapeutic use.

2. Description of Related Art

Factor XI or the precursor of plasma thromboplastin, is a glycoprotein that forms part of the contact phase, in the hemostasis mechanism, through its Factor IX activating effect and, on the other hand, of the fibrinolytic system through its plasminogen activating effect.

Factor XI deficiency is hereditary and is transmitted as a recessive autosomal character. This is a rare deficiency but one that is widespread in certain populations of the Middle East.

As with other factors in which a deficiency is rare (Factors V, XIII, X), therapeutic products purified from human plasma are nonexistent or rare, and the only replacement treatment is carried out using total plasma or the supernatant fraction of the cryoprecipitated plasma, but this entails the simultaneous injection of useless quantities of other plasma proteins, hence a risk of various major secondary reactions after multiple injections.

The purification of Factor XI, on an experimental scale, was difficult to achieve, and then, only with the use of powerful inhibitors, which suggests that this molecule is highly labile. Purification was carried out in a series of 4 or 5 steps of ion exchange chromatography and affinity chromatography, either starting from plasma (Bouma and Griffin, 1977, J. Biol. Chem. 252, 6432–6437) or from platelets (Schiffman and Yeh, 1990, Thromb. Res. 60, 87–97). A highly purified bovine Factor XI was also purified from 20 liters of plasma by precipitation and chromatographic steps in about 9 days (Koide et al., 1975, in: Methods in Enzymology—Blood Clotting Enzymes, pp. 65–73). Only one preparation having a quality compatible with therapeutic use has been described (Winkelman et al., 1988, Internat. Congress ISBT-BBTS London), and was obtained by adsorption on heparin-sepharose after recovery of Factors VIII and IX, but its specific activity does not exceed 5 U/mg of protein, and contains high doses of residual AT III. Applicants are aware of no other process of preparing Factor XI which allows for production on an industrial level, and which provides larger quantities of Factor XI of suitable quality for therapeutic use on a large scale.

SUMMARY OF THE INVENTION

Thus, the Applicants have sought to develop a new purification process suitable for very large volumes of plasma and making it possible to obtain, in a small number of steps that are easy to carry out on an industrial level, a Factor XI concentrate of suitable quality for therapeutic use.

The present invention thus relates to a human Factor XI concentrate, the preparation of which comprises only two steps: the first is a filtration-adsorption step which retains Factor XI quite selectively; after it has been desorbed, it is subjected to the second step, which involves chromatography on a cation exchange resin.

The Factor XI preparation may be further subjected to a conventional solvent-detergent viral inactivation treatment prior to the chromatography step, which serves to eliminate the residual products of this decontamination step completely.

The present method allows the production of therapeutic Factor XI from about 1100 liters of human plasma in a relatively short time (about 28 hours), that include the 8 hours - viral inactivation step.

DETAILED DESCRIPTION OF THE PREFERRED EMBODIMENTS

The purification process according to the present invention is applied to cryoprecipitated plasma supernatant which is obtained by conventional methods well known in the art and can be adapted to volumes of 1000 to 1200 liters.

The first purification step consists of filtering the cryoprecipitated plasma supernatant on a battery of 3 cartridges of filters, the porosity of which is between 0.5 and $2\mu$ and which are essentially negatively charged (Zeta plus TM CF filters supplied by Cuno, Process Filtration Products, a subsidiary of Commercial Intertech Corp., Meriden, CT, 06450, hereinafter designated "Cuno filters") which are described in U.S. Pat. Nos. 4,783,262 and 4,859,340. These filters are composed of perlites and purified cellulose having a small quantity of positively charged resin to retain particulate material, for example, having about 75% negative charges and 25% positive charges, and are completely free of asbestos and glass microfibers. Other commercially available filter systems can also be used.

The filters with adsorbed Factor XI are rinsed with a citrate/phosphate buffer solution comprising sodium citrate, disodium phosphate, potassium phosphate, sodium chloride and disodium EDTA and adjusted to a pH of between 5.5 and 6.5 and, preferably, to a pH of 6. This filtration step eliminates a large proportion of the plasmatic proteins.

The Factor XI, which has remained adsorbed on the layers of filters, owing to their negative charge, is desorbed therefrom by an increase in the ionic strength of the buffer solution by adjusting the final sodium chloride concentration. To this last buffer solution is also added a small quantity of antithrombin III (AT III) 0.1–0.2 U/ml, to protect the Factor XI from the action of the proteases.

The desorbed, dialyzed and concentrated fraction is then injected onto a chromatography column using a cation exchange resin, more particularly sepharose sulphate gel, equilibrated with a buffer solution composed of sodium citrate, sodium chloride, lysine and arginine, at a pH of 5.5 to 6.5, and preferably a pH of 6.

This column allows the remaining contaminant proteins and the viral inactivation agents to pass through.

It has been found by the present invention that sepharose sulphate gel has, unexpectedly, a very high Factor XI retention capacity (from 300 to 450 U/ml of gel), which makes it possible to avoid a subsequent ultrafiltration step which would lead to a loss of yield. In addition, the adsorption to the sepharose sulphate permits elution by practically physiological buffer solution, whereas the other resins (described earlier), which are sulphopropyl group based, necessitate more drastic conditions of elution.

After the column has been rinsed with the citrate/phosphate buffer comprising sodium citrate, disodium phosphate, potassium phosphate, sodium chloride, lysine and arginine, adjusted to a pH of between 6.1 and 6.9, and preferably to a pH of 6.5, the Factor XI is desorbed by increasing the pH of the buffer to between 7 and 8, and preferably to 7.5, and increasing the sodium chloride concentration to between 0.15 and 0.20 M, and preferably to 0.17.

As soon as it has been eluted, the Factor XI is stabilized by the addition of 0.5 to 3 U/ml high purity AT III and 0.5–4 U/ml heparin. Then the solution is sterilized by filtration, dispensed in vials and freeze dried by conventional methods.

The Factor XI obtained by the process according to the present invention has a specific activity at least equal to 100 U/mg of proteins.

The high purity of Factor XI obtained is demonstrated by electrophoresis on SDS-polyacrylamide gel, by biochemical analyses, and its harmlessness by biological tests on animals.

The Factor XI concentrate obtained using the process according to the present invention is thus particularly suitable for therapeutic use, in particular as a replacement therapy in cases of congenital or acquired deficiency in Factor XI.

The following example illustrates a form of embodiment of the present invention without, however, limiting the scope thereof.

EXAMPLE

Starting Material

Each batch of Factor XI is prepared from a volume of approximately 1000 liters of conventionally prepared human plasma cryoprecipitate supernatant. Cryoprecipitate supernatant is prepared by freezing fresh plasma at −60° C., gently thawing the frozen plasma at about 4° C., and centrifuging to separate the cryoprecipitate and the supernatant.

First Purification Step

The cryoprecipitate supernatant is passed over Zeta Plus Charged Filteraid cartridges arranged in batteries of three. Either the 0.5–1μ (type 50 S) or 1–2μ (type 30 S) filters can be used.

After removal of the filtrate containing a majority of the proteins of the cryoprecipitate supernatant, the cartridges are washed with a citrate/phosphate buffer solution comprising 5 mM of sodium citrate, 5 mM of disodium phosphate, 5 mM of potassium phosphate, 0.065 M of sodium chloride and 0.5 mM of disodium EDTA, and adjusted to a pH of 6 with citric acid.

A relatively selective adsorption of Factor XI on the layers of filters is observed.

The Factor XI is desorbed from the filters by increasing the ionic strength of the washing buffer by adjusting the NaCl concentration to 1 M. 0.2 U/ml of AT III are also added thereto to protect the Factor XI against the action of residual plasma proteases; the EDTA of the buffer solution also contributes to this protective action.

The Factor XI solution thus recovered is concentrated 30-fold and dialyzed to remove the EDTA, with the help of a Millipore TM ultrafiltration system formed of 10 cassettes with 10 K membranes.

The dialysis buffer solution is composed of 5 mM of sodium citrate, 0.14 M of sodium chloride, 5.5 mM of L-lysine and 20 mM of L-arginine, and adjusted to a pH of 6.

The dialyzed solution is passed over a DSLK2NLP (PALL TM) 0.45μ filter to clarify the solution and remove any bacterial contaminants.

Viral Inactivation Treatment

The solution containing the Factor XI is subjected to a solvent-detergent treatment known for its efficiency in destroying lipid enveloped type viruses (Horowitz et al., 1985, Transfusion 25, 516–522) and which includes incubation for 8 hours at 25° C. in the presence of 0.3% of tri-n-butyl-phosphate (TnBP) and 1% of Tween 80.

Second Purification Step

A chromatography column is used with a cation exchange resin, more particularly "sulfate-sepharose fast flow" TM gel (supplied by Pharmacia, Uppsala, Sweden).

The column is equilibrated with the dialysis buffer solution described above.

The column is equilibrated with the dialysis buffer solution described above.

After loading the column with the protein solution, the column is rinsed with 10 to 15 volumes of rinsing buffer solution to remove the slightly adsorbed proteins and the viral inactivating agents. This rinsing buffer comprises 10 mM of sodium citrate, 5 mM of disodium phosphate, 5 mM of potassium phosphate, 0.12 M of sodium chloride, 27 mM of lysine and 11.5 mM of arginine, at a pH of 6.5.

The linear flow rate of the equilibration, washing and elution buffers is 50 cm/h.

The Factor XI is eluted from the column by increasing the pH of the buffer to 7.5 and increasing the NaCl concentration to 0.17 M.

Upon elution of Factor XI, 2 U/ml of AT III (i.e. approximately 1.5 to 2.5% of the amount of FXI) and 2 U/ml of heparin (i.e. 1.5 to 2.5% of the amount of FXI) are added thereto to stabilize it. (Both products are of high purity and of a quality suitable for injection in humans.)

The Factor XI solution thus prepared is sterilized by filtration on a DSLKINFZP (PALL TM) 0.22μ filter, dispensed (10 ml/vial) and freeze dried.

Biochemical and Biologial Analyses of the Factor XI Concentrate

Six successive batches were analyzed.

The specific activity of Factor XI ranges from 130 to 150 U/mg of proteins (i.e. Factor XI+AT III). Before the addition of AT III, the specific activity is 210 U/mg.

The Factor XI, which had been adjusted to approximately 100–120 U/ml before freeze drying has a coagulating activity of 90 to 110 U/ml.

The following Tables 1 and 2 set forth the characteristics of the purified product.

TABLE 1

Factor XI recovery and purity of the purification fraction (mean values of 6 batches)

| FRACTIONS | YIELD (%) | SPECIFIC ACTIVITY (U/MG) | Purification Factor (fold) |
|---|---|---|---|
| Filteraid eluate | 37 | 12 | ≈800 |
| Solvent-detergent-treated | 98 | 12 | |

TABLE 1-continued

Factor XI recovery and purity of the purification fraction (mean values of 6 batches)

| FRACTIONS | YIELD (%) | SPECIFIC ACTIVITY (U/MG) | Purification Factor (fold) |
| --- | --- | --- | --- |
| fraction S-Sepharose eluate | 62 | 210 | ≈14000 |

TABLE 2

Characteristics of the freeze-dried Factor XI (mean values of 6 batches)

| | |
| --- | --- |
| Protein content (g/l) | 0.7–1.1 |
| Factor XI (U/ml) | 90–110 |
| Specific activity (U/mg) (after addition of AT III) | 130–150 |
| Cl-inhibitor* | 0.34 |
| Fibronectin* | 0.46 |
| alpha 2-macroglobulin* | 0.13 |
| IgG* | 0.17 |
| Albumin | <0.0006 |
| Fibrinogen | <0.002 |
| NAPPT (1/10 dilution) | >600" |
| NAPPT (1/100 dilution) | 221" |
| NAPPT (1/10)** | 166" |
| NAPPT 1/100)** | 216" |
| FCT (20° C.) | >24 h |
| FCT (37° C.) | >6 h |

*Expressed in mg/1000 U F XI
**Dilutions tested after heparin neutralization

As shown in Table 1, the adsorption step on the Filteraid layers allowed the separation of Factor XI from bulk of plasma protein resulting in 12 U Factor XI/mg protein. This specific activity represents about 800-fold purification factor from starting plasma. Chromatography on S-Sepharose of the partially purified Factor XI increased the specific activity to >200 U/mg corresponding to a purification factor of >14000 times from plasma. The washing step before elution of Factor XI, achieved by increasing the buffer pH, contributed to the improved purity by removing part of the contaminating proteins, mainly fibronectin. Under the conditions used, the gel capacity for Factor XI was about 300 U/ml and for proteins was approximately 36 mg/ml.

These results are to be compared with the therapeutic preparation of Winkelman et al. (Internat. Congr. ISBT-BBTS-London 1988, Abstract No. P.M.4.15) which has a specific activity of about 5 U/mg protein and contains equivalent doses of AT III.

The small quantity of protein contaminants (with the exception of the deliberately added AT III) is confirmed by immunonephelometry.

Electrophoresis on SDS-polyacrylamide gel shows a single major band at 160 KDa and a small band at 62 KDa which corresponds to the AT III. After reduction of the proteins with β-mercapto-ethanol, no band is detectable in the 50–30 KDa region, which shows that the Factor XI molecules have not been activated in the course of the purification process (Bouma and Griffin, 1986,Blood Coagulation, Ed. Hemker - pp 103–128).

The conventional methods are used to check carefully that there is no residual contamination by coagulation factors and constituents of the kinin system.

After reconstitution of the freeze dried product, conventional tolerance tests on animals are conducted:
thrombogenicity test on rabbits,
hypotension test on rats,
toxicity test on mice.

The test on rabbits shows that the product is not thrombogenic since the effective dose 50 (ED 50) is greater than 1000 U FXI/kg, while this same value ranges from 40 to 60 U/kg in the case of a PPSB concentrate, which is thus far more thrombogenic, and can effectively entail thromboses and disseminated intravascular coagulation when injected in high doses in man.

The concentration does not induce hypotension phenomena when intravenously injected into rats in doses of 50 U FXI/kg. This animal model is very sensitive to the presence of plasma components with vasoactive properties and demonstrates the absence of these components in the concentrate of Factor XI obtained using the process described.

When injected intravenously in mice in a high dose (2500 U FXI/kg), the Factor XI concentrate of the present invention does not induce any lethality or behavioral disturbance over a period of 7 days.

What is claimed is:

1. A process suitable for preparing a Factor XI concentrate on an industrial level having a specific activity at least equal to 100 U/mg of protein which comprises:
   (a) contacting a cryoprecipitate supernatant with a filter capable of adsorbing Factor XI to get filter adsorbed Factor XI;
   (b) desorbing said Factor XI from said filter to form a desorbed solution of Factor XI;
   (c) running said Factor XI through a single step chromatography column of a cation exchange resin to load said column with Factor XI; and
   (d) eluting said Factor XI to form said Factor XI concentrate.

2. The process of claim 1, wherein said filter is a series of filter cartridges of cellulose and perlites, having a porosity of 0.5 to 2μ and essentially negatively charged.

3. The process of claim 1, wherein step (a) is conducted by contacting said cryoprecipitate supernatant with said filter cartridges.

4. The process according to claim 1, which further comprises after step (a), rinsing said filter adsorbed Factor XI with a buffer solution which comprises sodium citrate, disodium phosphate, potassium phosphate, sodium chloride, disodium EDTA adjusted to a pH of 5.5 to 6.5.

5. The process according to claim 1, wherein in step (b), said Factor XI is desorbed from said filter by increasing the ionic strength of a buffer solution which comprises sodium citrate, disodium phosphate, potassium phosphate, sodium chloride, disodium EDTA and AT III.

6. The process according to claim 5, wherein said increasing the ionic strength is achieved by increasing the concentration of said sodium chloride to 0.5 to 2 M.

7. The process according to claim 1, which further comprises adding 0.1 to 0.2 U/ml of antithrombin III to said desorption buffer.

8. The process according to claim 1, which further comprises dialyzing said desorbed solution of Factor XI; concentrating said desorbed solution of Factor XI; and subjecting said desorbed solution of Factor XI to a viral inactivation treatment.

9. The process according to claim 1, wherein in step (c), said cation exchange resin is an agarose sulfated resin.

10. The process according to claim 1, which further comprises equilibrating said chromatography column with a buffer solution comprising sodium citrate, sodium chloride, lysine, and arginine adjusted to a pH of 5.5 to 6.5.

11. The process according to claim 1, which further comprises after step (c) rinsing said loaded column with a buffer solution which comprises sodium citrate, disodium phosphate, potassium phosphate, sodium chloride, lysine, and arginine, adjusted to a pH of 6.1 to 6.9.

12. The process according to claim 1, wherein step (d) comprises eluting said Factor XI by increasing the pH of the buffer to a value of between 7 and 8 and increasing the quantity of sodium chloride to a concentration of between 0.15 to 0.20 M.

13. The process according to claim 1, which further comprises after step (d), stabilizing said eluted Factor XI by adding 0.5 to 3 U/ml of antithrombin III and 0.5 to 4 U/ml of heparin per 100 U of Factor XI, and freeze drying said Factor XI concentrate.

* * * * *